(12) United States Patent
Rodenberg et al.

(10) Patent No.: US 9,149,585 B2
(45) Date of Patent: Oct. 6, 2015

(54) MULTI-NEEDLE INJECTION DEVICE

(71) Applicant: Cook Medical Technologies LLC, Bloomington, IN (US)

(72) Inventors: Jennifer Rodenberg, Lafayette, IN (US); William Bourdeau, Lafayette, IN (US); Charles Baxter, West Lafayette, IN (US); Steven Charlebois, West Lafayette, IN (US); Zach Wagner, Lafayette, IN (US); Sara Sherman, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 128 days.

(21) Appl. No.: 13/866,439

(22) Filed: Apr. 19, 2013

(65) Prior Publication Data

US 2013/0281930 A1  Oct. 24, 2013

Related U.S. Application Data

(60) Provisional application No. 61/636,091, filed on Apr. 20, 2012.

(51) Int. Cl.
*A61M 5/00* (2006.01)
*A61M 5/32* (2006.01)
*A61M 25/00* (2006.01)

(52) U.S. Cl.
CPC ......... *A61M 5/3295* (2013.01); *A61M 25/0084* (2013.01); *A61M 25/0097* (2013.01); *A61M 2025/0008* (2013.01); *A61M 2025/0086* (2013.01); *A61M 2025/0087* (2013.01)

(58) Field of Classification Search
CPC ............. A61M 2025/0008; A61M 2025/0086; A61M 2025/0087; A61M 25/0084; A61M 25/0097; A61M 5/3295

USPC ............................ 604/272, 164, 164.09, 173
See application file for complete search history.

(56) References Cited

U.S. PATENT DOCUMENTS 5,080,651 A   1/1992   Jullien
5,456,388 A   10/1995  Honstein et al.
(Continued)

FOREIGN PATENT DOCUMENTS

WO   WO 94/04220      3/1994
WO   WO 2011/150359 A1   12/2011

OTHER PUBLICATIONS

European Search Report from corresponding EP 13164738 dated Jul. 23, 2013 (3 pages).

*Primary Examiner* — Rebecca E Eisenberg
(74) *Attorney, Agent, or Firm* — Brinks Gilson & Lione

(57) ABSTRACT

A medical device and a method of treating stress urinary incontinence are provided. The device includes a cannula with a plurality of apertures. A plurality of needles is disposed within a lumen of the cannula. A handle includes a housing and a shifter mechanism to translate the plurality of needles from a first position in which the needles are disposed within the lumen of the cannula, to a second position in which a distal portion of each needle extends out of the lumen through respective apertures. The handle also includes a slot including a transversal track defining a potential range of rotational motion of the shifter mechanism with respect to the housing, and a plurality of longitudinal tracks defining a potential range of translational motion of the shifter mechanism with respect to the housing. The shifter mechanism may also rotate the cannula with respect to the handle.

20 Claims, 8 Drawing Sheets

(56) References Cited

U.S. PATENT DOCUMENTS

| | | |
|---|---|---|
| 6,001,089 A | 12/1999 | Burroughs et al. |
| 6,277,099 B1 | 8/2001 | Strowe et al. |
| 7,090,662 B2 | 8/2006 | Wimpenny et al. |
| 7,169,132 B2 | 1/2007 | Bendek et al. |
| 7,534,222 B2 | 5/2009 | Sugita et al. |
| 2002/0143302 A1* | 10/2002 | Hinchliffe et al. ............ 604/272 |
| 2007/0255306 A1 | 11/2007 | Conlon et al. |
| 2008/0154235 A1 | 6/2008 | Cohen |
| 2009/0318891 A1 | 12/2009 | Marcotte et al. |
| 2010/0217231 A1 | 8/2010 | Ilan et al. |
| 2010/0268189 A1 | 10/2010 | Byrnes et al. |
| 2010/0330589 A1 | 12/2010 | Bahrami et al. |
| 2011/0009848 A1* | 1/2011 | Woodard et al. .............. 604/511 |
| 2011/0015576 A1 | 1/2011 | Plumptre et al. |
| 2011/0060310 A1 | 3/2011 | Prestrelski et al. |

\* cited by examiner

MULTI-NEEDLE INJECTION DEVICE

CROSS-REFERENCE TO RELATED APPLICATIONS

This application claims priority and the benefit of provisional U.S. Application Ser. No. 61/636,091, filed Apr. 20, 2012, which is incorporated herein by reference in its entirety.

TECHNICAL FIELD

This disclosure relates to devices suitable for treating Stress Urinary Incontinence ("SUI"). Patients suffering from SUI are unable to control the release of urine during certain movements such as coughing, laughing, sneezing or exercising. SUI may be caused by the weakening of the pelvic floor muscles, such as the fascia supporting the urethra. In women, SUI has been associated with physical changes resulting from pregnancy, childbirth, and menopause. Several treatments are known for SUI, including placing a sling under the urethra, inserting a pessary into female patient's vagina, surgery, or injecting bulking agents into the tissue surrounding the urethra.

BRIEF SUMMARY

A first representative embodiment of the disclosure provides a medical device. The medical device includes an elongate cannula comprising a distal end portion, a proximal end portion, a lumen defined therethrough, and a plurality of apertures disposed through the distal end portion to provide communication with the lumen. The medical device additionally includes a plurality of injection needles disposed within the lumen. Each needle includes a distal portion disposed in alignment with the plurality of apertures, and a proximal end portion. The medical device additionally comprises a handle fixed with respect to the cannula. The handle includes a housing configured to enclose a fluid volume, a shifter mechanism coupled to the proximal end portion of the cannula and the proximal end portion of each of the plurality of needles, a slot defined in the housing configured to receive a portion of the shifter mechanism therethrough, and a conduit providing fluid communication between the fluid volume and the cannula. The shifter mechanism is translatable with respect to the housing to translate the plurality of needles from a first position to a second position. The shifter mechanism is further rotatable with respect to the handle to rotate the cannula with respect to the handle. The slot includes a transversal track and a plurality of longitudinal tracks. The transversal track defines a potential range of rotational motion of the shifter mechanism with respect to the housing, and each longitudinal track defines a potential range of translational motion of the shifter mechanism with respect to the housing between the first and second positions. In the first position the distal portion of each of the plurality of needles is disposed within the lumen of the cannula, and in the second position the distal portion of each of the plurality of needles extends out of the lumen through respective apertures.

A second representative embodiment of the disclosure provides a medical device. The medical device includes an elongate cannula comprising a distal end portion, a proximal end portion, a lumen defined therethrough, and a plurality of apertures disposed through the distal end portion to provide communication with the lumen. The medical device additionally includes a plurality of injection needles disposed within the lumen. Each needle includes a distal portion disposed in alignment with the plurality of apertures, and a proximal end portion. The medical device additionally comprises a handle fixed with respect to the cannula. The handle includes a housing configured to enclose a syringe enclosing a fluid volume, a shifter mechanism coupled to the proximal end portion of the cannula and the proximal end portion of each of the plurality of needles, a slot defined in the housing configured to receive a portion of the shifter mechanism therethrough, a syringe actuation mechanism, and a conduit providing fluid communication between the fluid volume and the cannula. The shifter mechanism is translatable with respect to the housing to translate the plurality of needles from a first position to a second position. The shifter mechanism is further rotatable with respect to the handle to rotate the cannula with respect to the handle. The slot includes a transversal track and a plurality of longitudinal tracks. The transversal track defines a potential range of rotational motion of the shifter mechanism with respect to the housing, and each longitudinal track defines a potential range of translational motion of the shifter mechanism with respect to the housing between the first and second positions. In the first position the distal portion of each of the plurality of needles is disposed within the lumen of the cannula, and in the second position the distal portion of each of the plurality of needles extends out of the lumen through respective apertures. The syringe actuation mechanism includes a thumbwheel, a first tubular portion affixed to the thumbwheel, and a second tubular portion configured to engage the first tubular portion and to partially receive the syringe. Rotation of the thumbwheel produces a translational motion of the second tubular portion towards the proximal end of the housing, urging expulsion of the fluid volume from the syringe and out of the needles.

A third representative embodiment of the disclosure provides a method to treat urinary stress incontinence. The method includes the step of providing a device with an elongate cannula with a plurality of apertures disposed upon a distal end thereof. The device includes a plurality of needles that each extend through a lumen in the cannula and selectively extend from each of the plurality of apertures. A handle is manipulable to urge the plurality of needles to extend outward from the apertures, and to rotate the cannula and the needles with respect to the handle. The method additionally includes the steps of inserting the device into the patient in a first position, manipulating the handle to extend the plurality of needles through the apertures, expelling fluid from the plurality of needles, and retracting the plurality of needles into the cannula. The method further includes the steps of manipulating the handle to rotate the cannula and the needles into a second position within the patient, extending the plurality of needles through the apertures, and expelling additional fluid from the plurality of needles.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Figure 1:
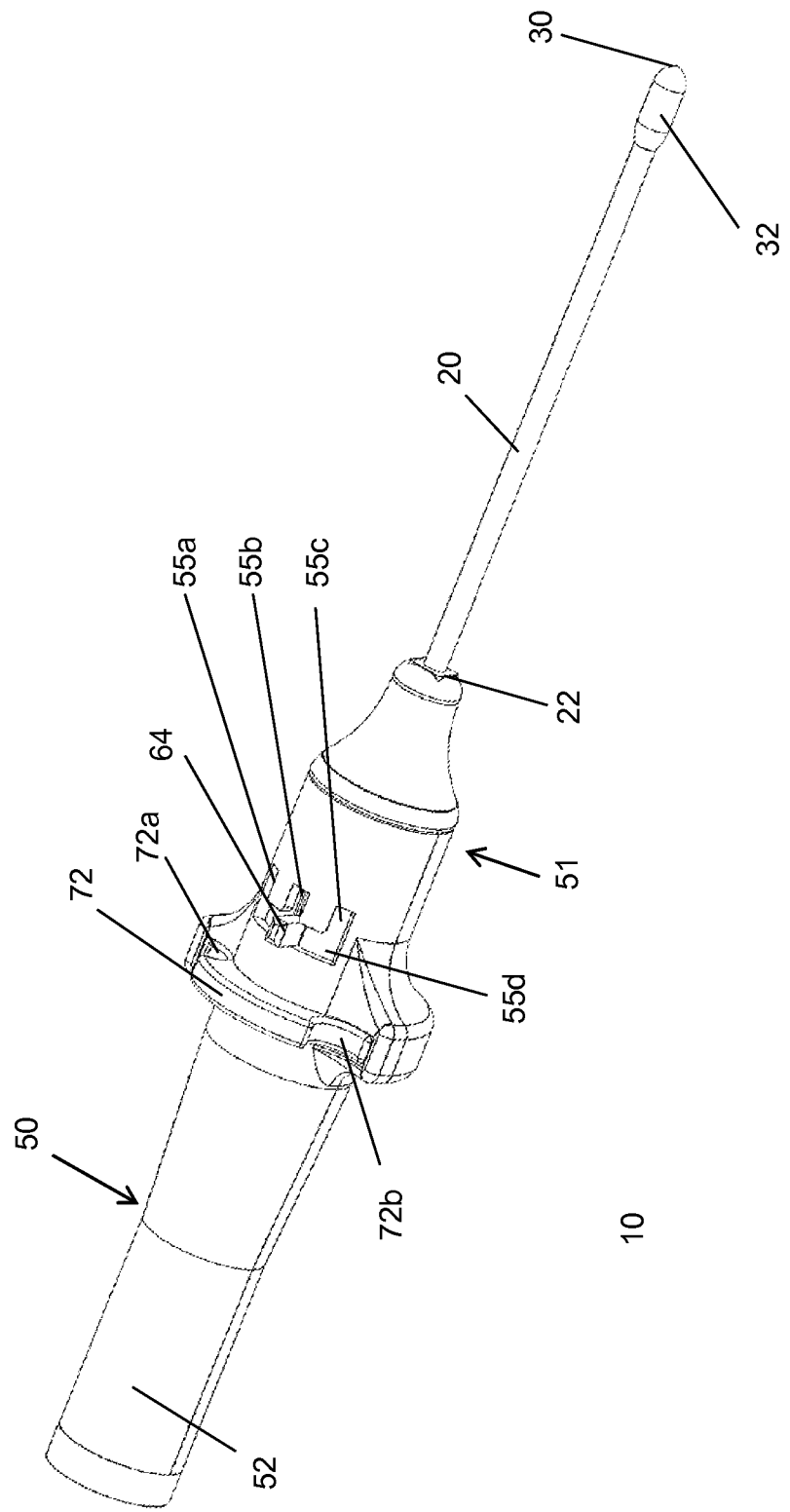
FIG. 1 is a perspective view of a multi-needle injection device.
Figure 2:
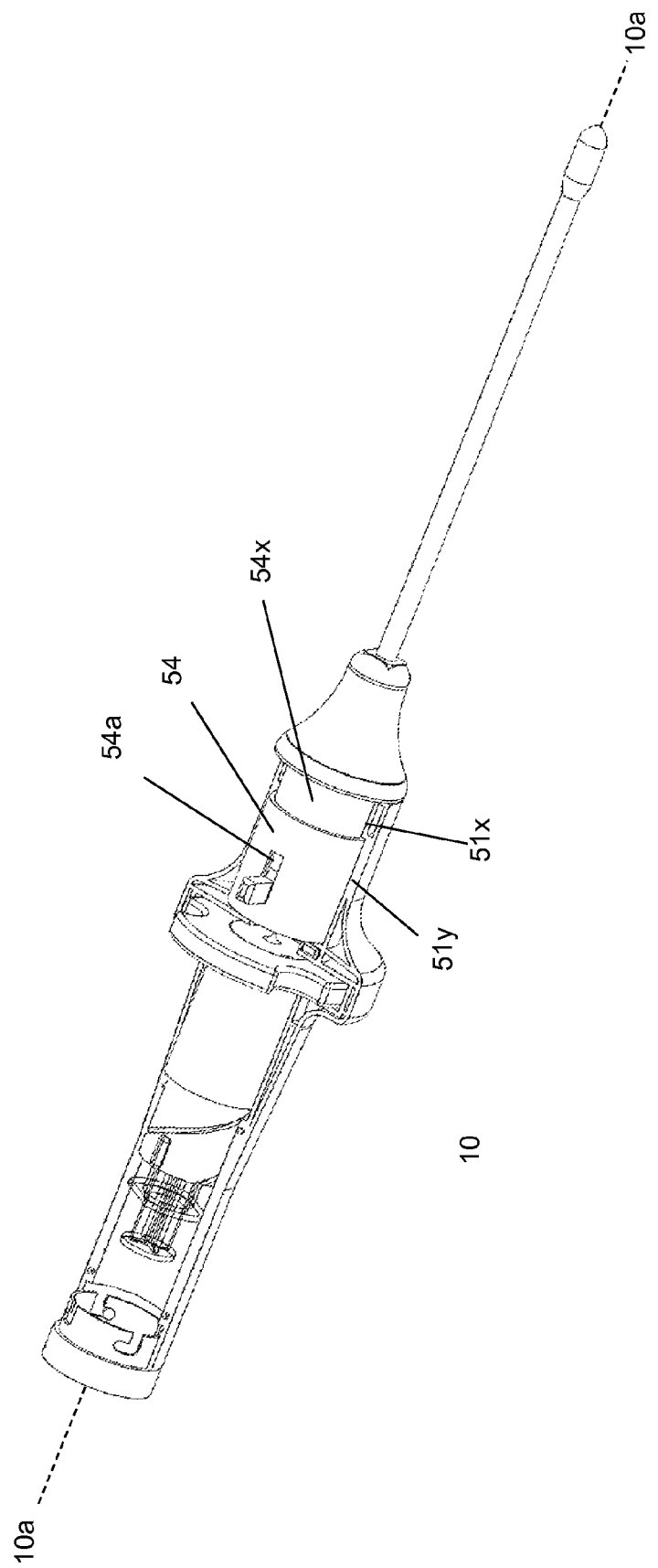
FIG. 2 is a perspective view of the multi-needle injection device of FIG. 1 with the top housing removed.
Figure 3:
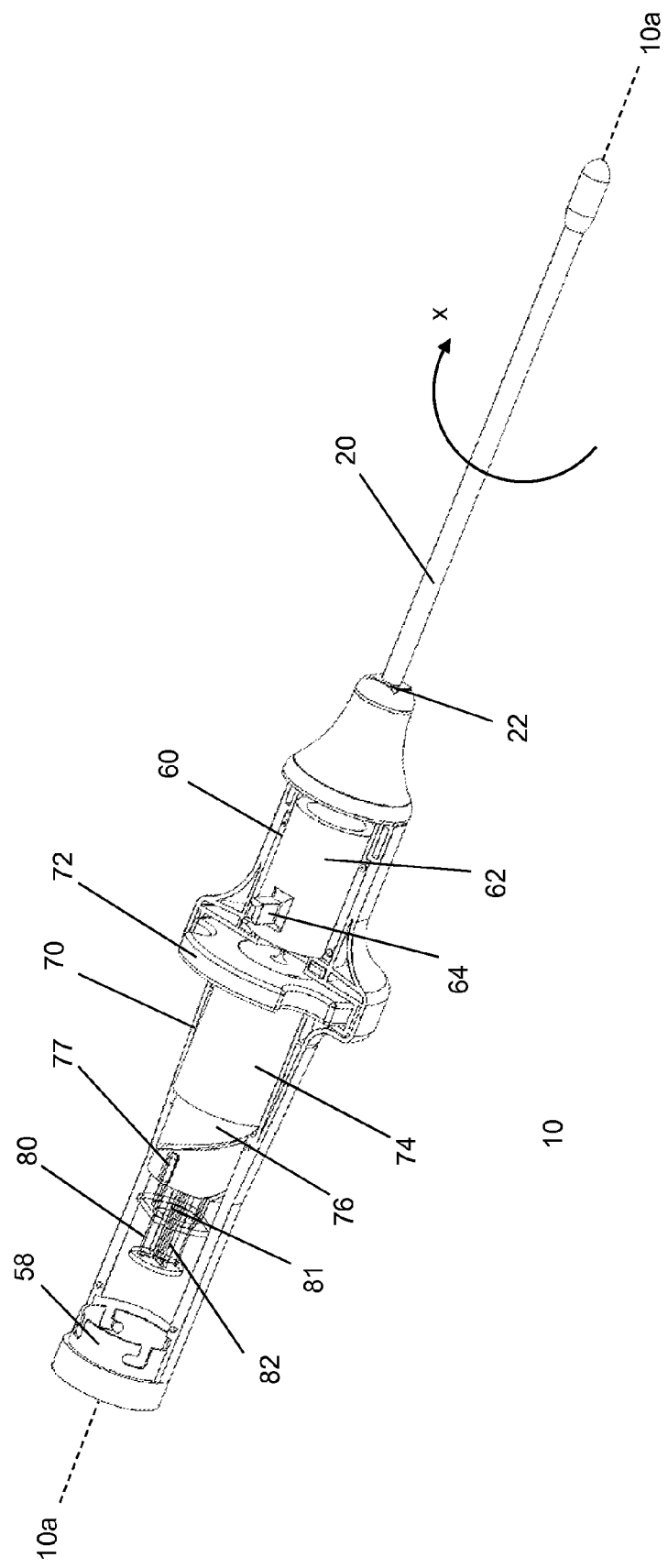
FIG. 3 is a perspective view of the multi-needle injection device of FIG. 1 with the top housing and the coupling element removed.

Turning now to FIGS. 1-9, a fluid injection device 10 suitable for various medical procedures is provided. In some embodiments, the device 10 may be suitable for injecting therapeutic agents, such as cell-based media or agents or other injection media, into the tissue coaxially surrounding a female urethra in an attempt to strengthen the tissue therein to prevent or reduce the effects of stress urinary incontinence. In other embodiments, the device 10 may be used in other portions of the human or mammal anatomy to inject therapeutic agents simultaneously at multiple predetermined or reliable locations within the patient. The device 10 is configured to be inserted into a patient through an available orifice, such as directly into female urethra. As can be appreciated, the embodiment discussed in detail below is configured for insertion in the patient's urethra, but the device 10 can be otherwise sized and shaped to be specifically configured for other anatomical locations and procedures without departing from the scope of this disclosure.

The device 10 includes an elongate relatively flexible cannula 20, and a handle 50 that is fixed to a portion of the cannula 20. A plurality of needles 41, 42, 43 are movably disposed within a lumen 26 of the cannula 20. The cannula 20 further includes a distal end portion 30 that includes a plurality of apertures 34a, 34b, 34c disposed therethrough to provide communication with the lumen 26. Each of the plurality of needles 41, 42, 43 are disposed within the cannula 20 to be aligned with a respective one of the plurality of apertures 34a, 34b, 34c.

The cannula 20 is an elongate flexible member that spans between the distal end portion 30 and a proximal end portion 22. In some embodiments, the distal end portion 30 may be made from a bulb 32 or closed tube that is connected to a distal end of the cannula 20. The bulb 32 includes a lumen 33 defined at the proximal end portion thereof that allows communication with the lumen 26 of the cannula 20 when the bulb 32 is fixed to a distal end of the cannula 20.

The apertures 34a, 34b, 34c are each disposed at various locations about the outer circumferential surface of the bulb 32. The apertures 34a, 34b, 34c may be disposed at about the 3 o'clock position, the 6 o'clock position, and the 9 o'clock position, respectively, if the distal end of the bulb 32 is considered to be the face of a conventional analog clock. In some embodiments, the apertures are disposed such that no aperture is provided at about the 12 o'clock position. In some embodiments, the first and third apertures 34a, 34c are each disposed substantially equidistant from the second aperture 34b upon the outer circumferential surface of the bulb 32.

In other embodiments, the outer circumferential surface of the cannula 20 is divided into upper, right, bottom, and left quadrants, each quadrant covering about a fourth of the outer circumferential surface of the cannula 20. In some embodiments, an aperture (e.g. 34a) is disposed upon the right quadrant, an aperture is disposed upon the bottom quadrant, and an aperture is disposed upon the left quadrant, and no apertures are disposed upon the upper quadrant.

The apertures 34a, 34b, 34c are disposed upon the bulb 32 to accurately position the needles 41, 42, 43 projecting therefrom into a desired pattern from the bulb 32. In embodiments where the device 10 is contemplated to be used to inject therapeutic agents into the muscular tissue surrounding a female patient's urethra for the treatment of or prevention of stress induced incontinence, it is often necessary that fluid not be injected through the anterior portion of the urethra (i.e. the portion of the urethra that runs closest to the front of the body) because blood vessels and nerve bundles are disposed proximate to the urethra in this area. Accordingly, the bulb 32 upon the cannula 20 is configured with apertures at three (or other numbers of multiple locations) locations for needles 41, 42, 43 to exit the cannula 20 to substantially simultaneously enter the tissue (submucosa and musculature) coaxially surrounding the urethra but remote from the upper portion of the urethra. Once the needles pierce and are positioned within the tissue, the device 10 can be manipulated to simultaneously inject therapeutic agents into the muscle tissue while avoiding injection into the upper portion of the urethra.

The plurality of apertures 34a, 34b, 34c are each fluidly connected to the lumen 33 of the bulb 32 (and ultimately to the lumen 26 of the cannula 20) with respective angled sublumens 35a, 35b, 35c that each provide for transmission of one of the plurality of needles (discussed below) disposed therethrough. In some embodiments, each of the sublumens may be disposed at an acute angle α with respect to a longitudinal axis 10a of the device at the distal end portion 30 of the cannula 20. For example, in some embodiments, the sublumens 35a, 35b, 35c may be disposed at an angle α of about 35 degrees, 40 degrees, 45 degrees to the longitudinal axis 10a, or other appropriate angles within the range of about 20 degrees to about 60 degrees with respect to the longitudinal axis 10a.

Distal end portions 41a, 42a, 43a of each of the needles 41, 42, 43, respectively, may be configured to be curved or bent with respect to the remainder of the needle. In some embodiments, the distal end portions 41a, 42a, 43a may each be bent or angled to form an acute angle β with respect to the proximal and central portions of the respective needle. In some embodiments, the angle β may be about 40 degrees, about 20 degrees, about 30 degrees, or at suitable angles within the range of about 20 and about 60 degrees. In some embodiments, the bend angle β of the distal end portion of the respective needle 41, 42, 43 may be substantially the same as the angle α that the respective sublumens 35a, 35b, 35c form of the bulb with respect to a longitudinal axis of the cannula 20 through the bulb 30. In other embodiments, the angles β and α may be slightly different, such as an embodiment specifically depicted in the figures showing the sublumen angle of about 35 degrees and a bend angle of the needle of about 40 degrees. In this embodiment (and other embodiments where the angles α and β are not exactly the same), the needle presses or moves against at least a portion of the inner surface of the respective sublumen 35a, 35b, 35c, which increases the friction between the needle and the bulb, therefore preventing unintended motion of the needles within the cannula due to unintended external forces placed thereon. The plurality of needles 41, 42, 43 may be made from strong and flexible materials capable of being configured with a lumen and capable of maintaining a sharpened tip. In some embodiments, the needles 41, 42, 43 may be stainless steel, while in other embodiments the needles may be Nitinol or various alloys thereof.

The handle 50 may include a housing 52 formed from an upper clamshell half 52a and a lower clamshell half 52b that may be opened and closed by an user. The housing 52 may include a distal housing section 51 and a proximal housing section 53.

In some embodiments, a shifter mechanism 60 is disposed within the housing distal section 51. The shifter mechanism 60 may include a cylindrical portion 62 with a projection 64 extending outward from the inner cylindrical portion 62. The distal housing section 51 may include a slot 55 to allow the projection 64 to extend beyond an outer surface of the distal housing section 51.

The needles 41, 42, 43 are movably disposed within the lumen of the cannula 20 and the bulb 32. The needles 41, 42, 43 are each fixed to a shifter mechanism 60. The shifter mechanism 60 may be linearly translated with respect to the housing 52 of the handle 50, which causes the plurality of needles 41, 42, 43 to translate within the lumen 26 of the cannula 20. When the shifter mechanism 60 is in a first position, distal tips 41b, 42b, 43b of the respective plurality of needles 41, 42, 43 are disposed within the apertures 34a, 34b, 34c just inside of the outer circumferential surface of the distal end portion 30 of the cannula 20. When the shifter mechanism 60 is in a second position the distal tips 41b, 42b, 43b of the needles 41, 42, 43 extend outward from the apertures 34a, 34b, 34c and the outer circumferential surface of the cannula 20 to be interacted with, and be inserted into, tissue proximate to the distal end portion 30 of the cannula 20.

Figure 8:
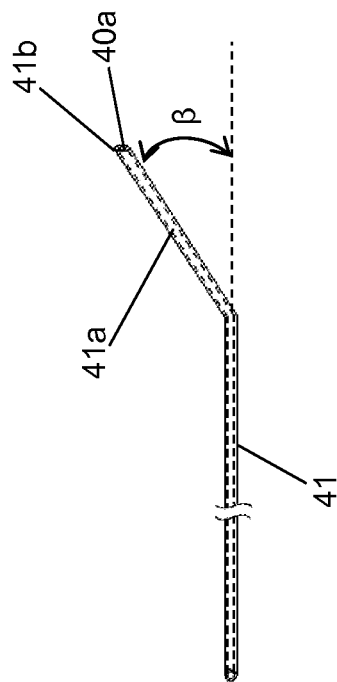
FIG. 8 is a side view of a needle of the device of FIG. 1.

As shown in FIG. 8, each needle 41, 42, 43 includes a lumen 40a along its length to allow liquid, such as therapeutic agents, to flow therethrough and exit the respective needle 41, 42, 43 through the distal tip 41b, 42b, 43b thereon. In some embodiments, the distal tips 41b, 42b, 43b may include a sharpened point thereon and a beveled edge that allows the distal tip 41b, 42b, 43b to easily pierce the patient's tissue with movement or force applied to the needle 41, 42, 43 by the device 10, and specifically the relative movement of the shifter mechanism 60. The distal end portions 41a, 42a, 43a of the needles are configured to be disposed within the respective sublumens 35a etc. of the bulb 32, with the distal tip 41b, 42b, 43b of each needle 41, 42, 43 disposed just below the outer circumferential surface of the bulb 32 when the shifter mechanism 60 is in the first position. When the shifter mechanism 60 reaches the second position, the distal tips 41b, 42b, 43b and distal end portions 41a, 42a, 43a of the plurality of needles 41, 42, 43 each simultaneously extend from and out of the respective apertures 34a, 34b, 34c upon the bulb 32.

In some embodiments, the distal housing section 51 may have a distal portion 51x and a proximal portion 51y. An inner diameter of the distal portion 51x may be smaller than an inner diameter of the proximal portion 51y. The handle may also include a coupling element 54 disposed within the distal housing section 51. The coupling element 54 may surround the cylindrical portion 62 of the shifter mechanism 60, and include an opening 54a through which the projection 64 may fit.

A proximal portion of the coupling element 54 may have a cylindrical profile with an inner diameter just bigger than an outer diameter of the cylindrical portion 62 of the shifter 60, to allow the coupling element 54 to slide or rotate with respect to the shifter 60. A distal portion of the coupling element 54 may have a tapered profile. The opening 54a may have a profile that allows an user to translate the shifter mechanism 60 longitudinally (parallel to the longitudinal axis 10a of the device 10) with respect to the coupling element 54 by actuation of the projection 64. The opening 54a may have a profile that does not allow rotational translation of the shifter mechanism 60 with respect to the coupling element 54, such that actuation of the shifter mechanism in a direction orthogonal to axis 10a would result in the coupling element 54 being rotated in the same direction.

The cylindrical proximal portion of the coupling element 54 may have a distal section 54x and a proximal section 54y. The outer diameter of the distal section 54x may be just smaller than an inner diameter of the distal portion 51x of the distal housing section 51. In turn, the outer diameter of the proximal section 54y may be just smaller than an inner diameter of the proximal portion 51y of the distal housing section 51. Thus the coupling element 54 may rotate with respect to the distal housing section 51, but it may not translate longitudinally (parallel to axis 10a of the device 10) with respect to the housing 52.

In some embodiments, the slot 55 of the distal housing section 51 may have an E-shape (FIG. 5) including a plurality of longitudinal tracks 55a, 55b, 55c aligned in parallel to the longitudinal axis 10a of the device 10. The slot 55 may also include a transversal track 55d disposed at a substantially orthogonal angle with respect to the plurality of longitudinal tracks 55a, 55b, 55c. The length of the longitudinal tracks 55a, 55b, 55c defines the potential length of travel of the shifter mechanism 60 relative to the housing 52, and thus the distance that the needles 41, 42, 43 may extend from their respective apertures 34a, 34b, 34c in the cannula 20 when the shifter mechanism 60 is in the second position. The length of the transversal track 55d defines the potential degree of rotation of the shifter mechanism 60 relative to the housing 52, as well as the potential degree of rotation of the cylindrical portion 54 relative to the housing.

The proximal end portion 22 of the cannula 20 is fixed to the distal end of the coupling element 54. When a user rotates the shifter mechanism 60 by actuating the projection 64 along the transversal track 54d, the corresponding rotation of the coupling element 54 results in a corresponding rotation of the cannula 20. In other words, a user may deploy the needles 41, 42, 43 by actuating the projection 64 in a direction parallel to the axis 10a of the device 10, and the user may rotate the cannula 20 by actuating the projection 64 in a direction orthogonal to the axis 10a of the device 10.

Figure 4:
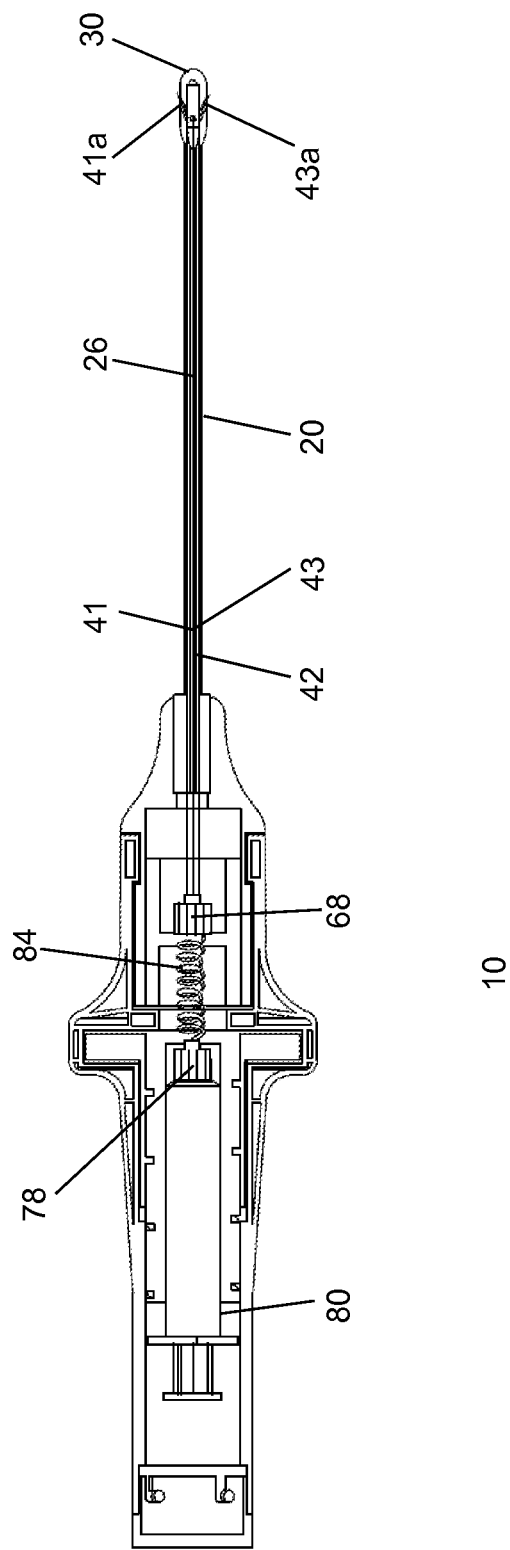
FIG. 4 is a top cross-sectional view of the multi-needle injection device of FIG.
Figure 5:
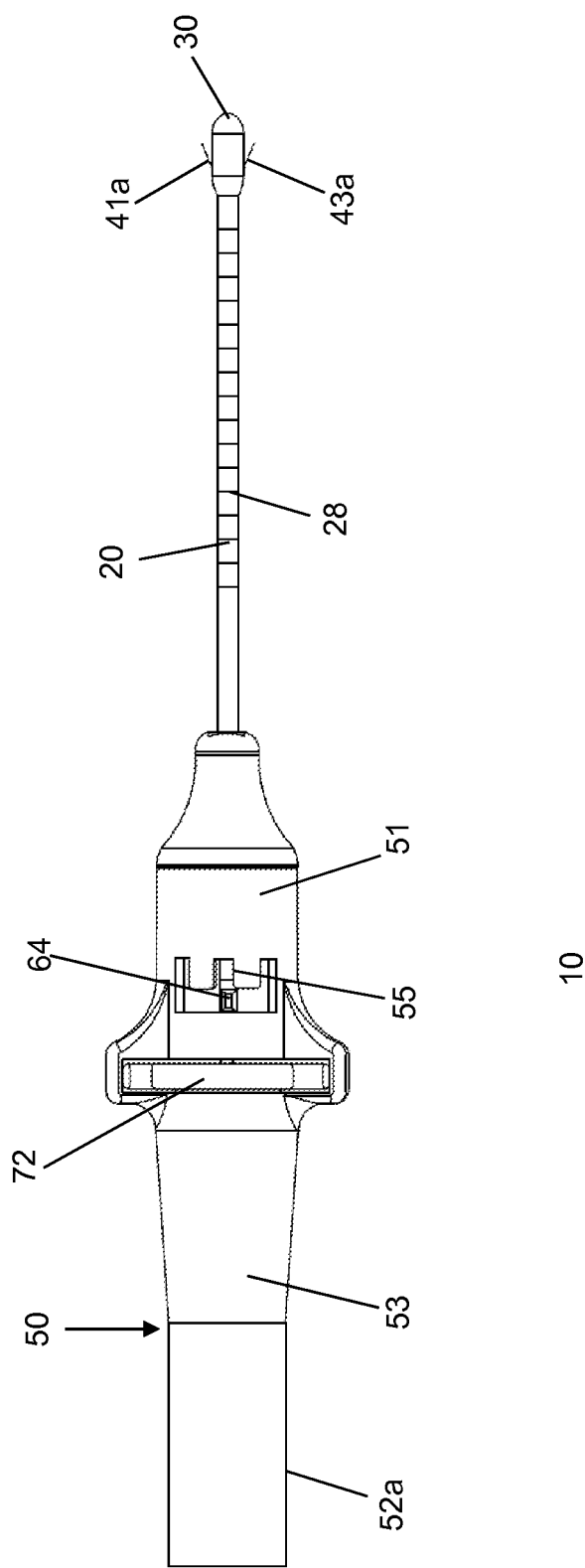
FIG. 5 is a top view of the multi-needle injection device of FIG. 1.
Figure 6:
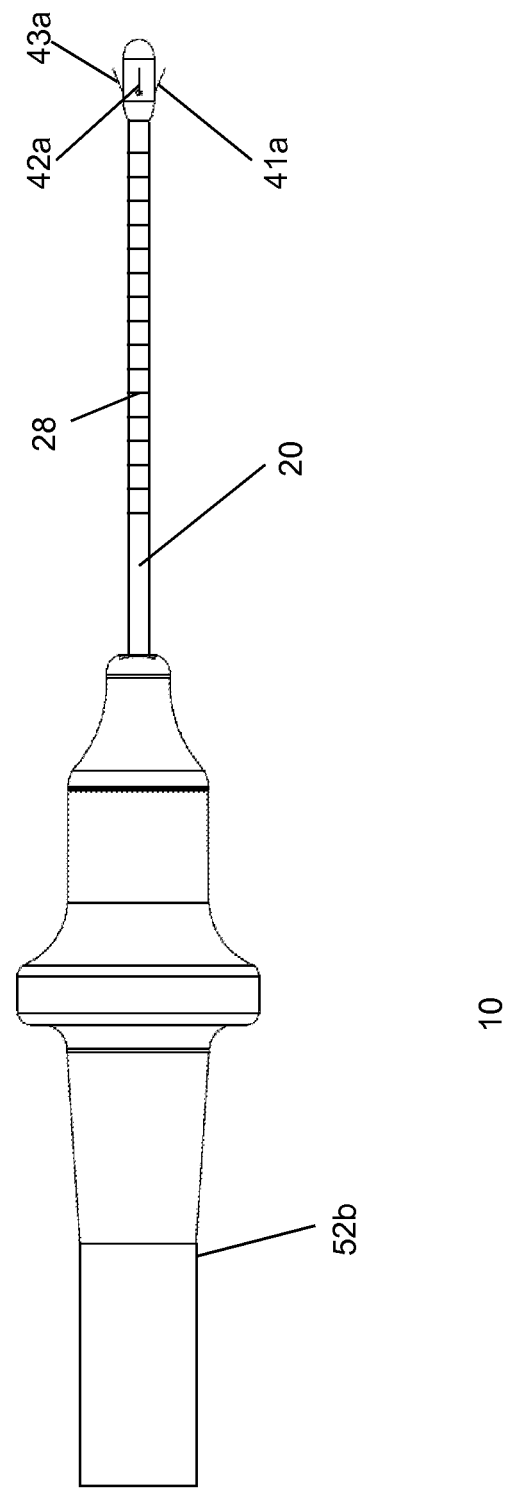
FIG. 6 is a bottom view of the multi-needle injection device of FIG. 1.
Figure 7:
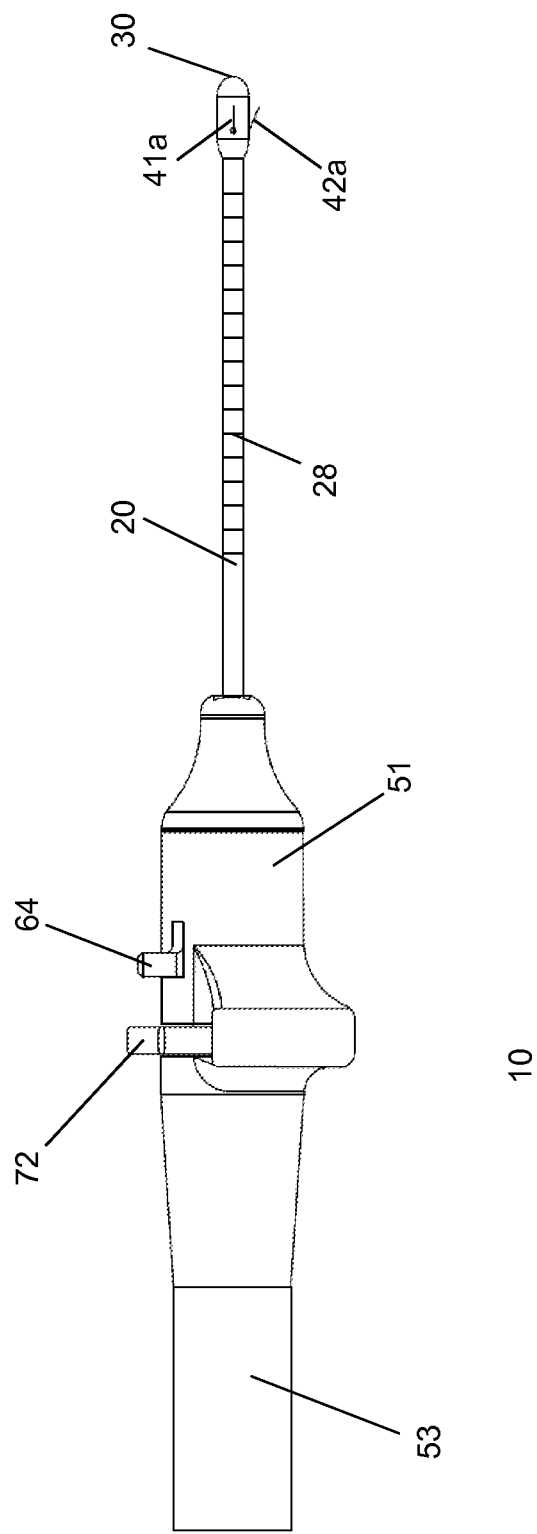
FIG. 7 is a right-side view of the multi-needle injection device of FIG. 1.
Figure 9:
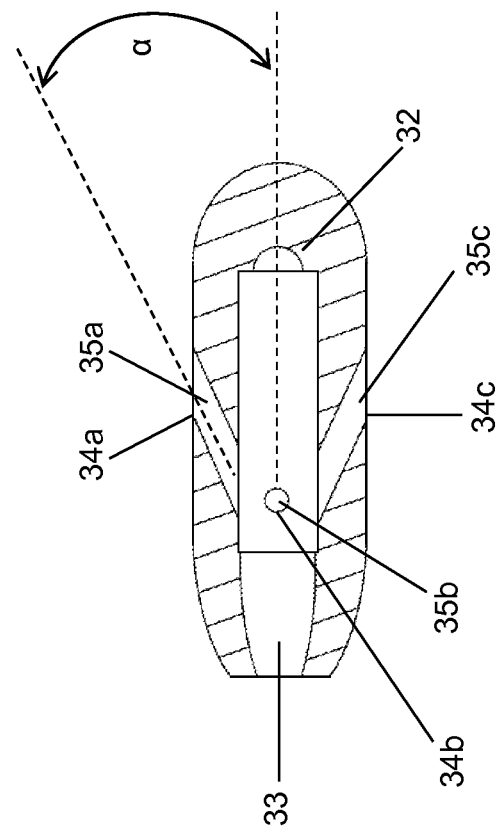
FIG. 9 is a cross-sectional view of the bulb of the device of FIG. 1

In some embodiments, the handle 50 may include a syringe actuation mechanism 70 disposed within the proximal housing section 53. The syringe actuation mechanism may be configured to receive a syringe 80 as shown in FIG. 4. The syringe actuation mechanism 70 may comprise a thumbwheel 72 fixed to a first tubular portion 74. The syringe actuation mechanism 70 may also include a second tubular portion 76 configured to receive the syringe 80. The first and second tubular portions 74, 76 may be hollow, and of a diameter sufficient to permit the second tubular portion 76 to slide within the first tubular portion 74. An inner surface of the first tubular portion 74 may include a threaded profile configured to engage a threaded profile of an outer surface of the second tubular portion 76. The outer tubular portion 76 may also include one or more protrusions 77 configured to engage one or more tracks of an inner surface of the proximal housing portion 53 of the handle 50.

The thumbwheel 72 may be partially enclosed by the housing 52, with a portion of the thumbwheel 72 accessible via an opening 56 of the housing 52. In some embodiments, the thumbwheel may include indentations 72a, 72b, 72c equally spaced along a circumferential profile of the thumbwheel 72.

The syringe 80 includes a fluid chamber 81 and a plunger 82. The fluid chamber 81 is fixed with respect to the second tubular portion 76. In an initial position, the plunger 82 may be pivoted away from the fluid chamber 81, and the second tubular portion 76 partially inserted into the first tubular portion 74. As the thumbwheel 72 is rotated in a clockwise direction x, a corresponding rotation of the first tubular portion 74 results in a translational motion of the second tubular portion 76 towards a cap 58 at the proximal end of the handle 50. The translational motion of the second tubular portion 76 is the result of the one or more protrusions 77 engaging the one or more tracks in the inner surface of the housing 53, which prevents rotation of the second tubular portion 76. As the second tubular portion 76 and the fluid chamber 81 of the syringe 80 advance within the housing 52 toward the proximal end of the handle 50, the plunger 82 remains stationary with respect to the housing 52 as it contacts the cap 58.

The syringe actuation mechanism 70 may comprise a first luer lock adaptor 78 disposed within and passing through a proximal end of the syringe actuation mechanism 70. The first luer lock adaptor 78 may be connected to a flexible fluid conduit 84 allowing fluid communication between the first luer lock adaptor 78 and a second luer lock adaptor 68 disposed within and passing through a proximal end of the shifter mechanism 60. The proximal ends of each of the needles 41, 42, 43 are passed through holes formed in the second luer lock adaptor 68 and glued (or otherwise fixed) thereto to fix the needles 41, 42, 43 to the shifter mechanism 60. The open proximal tips of each needle 41, 42, 43 extend into the second luer lock adaptor 68 such that fluid that passes into the first luer lock adaptor 78, the flexible fluid conduit 84 and the second luer lock adaptor 68 may flow into the lumen of each needle 41, 42, 43 and ultimately from the tip 41b, 42b, 43b of each needle.

The spacing and inclination of the threaded profiles of the inner surface of the first tubular portion 74 and the outer surface of the second tubular portion 76 may be configured such that a 360-degree rotation of the thumbwheel 72 results in a full depression of the plunger 82 within the fluid chamber 81 of the syringe 80. Thus each 120-degree rotation of the thumbwheel 72 results in a third of a dose contained in the syringe 80 being dispensed.

The cannula 20 may include a plurality of visually perceptible indicator lines 28 thereon that allow the physician to properly position at appropriate depth within the patient. The indicator lines 28 may be painted, etched, coated, scribed, or otherwise marked or disposed upon an outer surface of the cannula 20. In other embodiments, the indicator lines 28 may be or include tactile features upon the outer circumferential surface of the cannula 20, such as indentations, ridges, roughened areas, etc. In some embodiments, the indicator lines 28 may be equally spaced in 1 cm increments along the length of the cannula 20 and completely surrounding the circumference of the cannula 20.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

The invention claimed is:

1. A medical device comprising:
  an elongate cannula comprising:
    a distal end portion;
    a proximal end portion;
    a lumen defined therethrough; and
    a plurality of apertures disposed through the distal end portion to provide communication with the lumen;
  a plurality of injection needles disposed within the lumen, each comprising:
    a distal portion disposed in alignment with the plurality of apertures; and
    a proximal end portion;
  a handle fixed with respect to the cannula, the handle comprising:
    a housing configured to enclose a fluid volume;
    a shifter mechanism coupled to the proximal end portion of the cannula and the proximal end portion of each of the plurality of needles, the shifter mechanism translatable with respect to the housing to translate the plurality of needles from a first position to a second position, the shifter mechanism rotatable with respect to the handle to rotate the cannula with respect to the handle;
    a slot defined in the housing configured to receive a portion of the shifter mechanism therethrough, the slot comprising a transversal track and a plurality of longitudinal tracks, wherein the transversal track defines a potential range of rotational motion of the shifter mechanism with respect to the housing, and each longitudinal track defines a potential range of translational motion of the shifter mechanism with respect to the housing between the first and second positions; and
    a conduit providing fluid communication between the fluid volume and the cannula;
  wherein in the first position the distal portion of each of the plurality of needles is disposed within the lumen of the cannula; and
  wherein in the second position the distal portion of each of the plurality of needles extends out of the lumen through respective apertures.

2. The medical device of claim 1, wherein the cannula further comprises a plurality of visually perceptible indicators configured to provide an indication of depth of insertion of the cannula within a patient.

3. The medical device of claim 1, wherein an outer circumferential surface of the distal end portion of the cannula defines an upper portion, a right side portion, a bottom portion, and a left side portion each substantially equally spaced from their respective neighboring portion around the circumferential surface of the cannula.

4. The medical device of claim 3, wherein
  a first of the plurality of apertures is disposed on the right side portion;
  a second of the plurality of apertures is disposed on the bottom portion; and
  a third of the plurality of apertures is disposed on the left side portion.

5. The medical device of claim 3, wherein the device is configured to be inserted into the patient's urethra with the upper portion of the cannula facing upwardly when the patient is oriented in a lithotomy position.

6. The medical device of claim 1, wherein the plurality of needles are configured to extend from the distal portion of the cannula multiple times while the device is inserted into a patient.

7. The medical device of claim 1, wherein the housing is configured to enclose a syringe enclosing the fluid volume.

8. The medical device of claim 7, the handle further comprising:
  a syringe actuation mechanism comprising:

a thumbwheel;
a first tubular portion affixed to the thumbwheel; and
a second tubular portion configured to engage the first tubular portion and to partially receive the syringe.

9. The medical device of claim 8, wherein rotation of the thumbwheel produces a translational motion of the second tubular portion towards the proximal end of the housing, urging expulsion of the fluid volume from the syringe and out of the needles.

10. The medical device of claim 1, wherein the plurality of needles are configured to extent linearly about 7 mm from their respective aperture, and each needle exits their respective aperture at about a 40 degree angle with respect to a longitudinal axis of the cannula.

11. A method for treating stress urinary incontinence, comprising:
providing a device with an elongate cannula with a plurality of apertures disposed upon a distal end thereof, a plurality of needles that each extend through a lumen in the cannula and selectively extend from each of the plurality of apertures, a handle manipulable to urge the plurality of needles to extend outward from the apertures, and to rotate the cannula and the needles with respect to the handle;
inserting the device into the patient in a first position;
manipulating the handle to extend the plurality of needles through the apertures;
expelling fluid from the plurality of needles;
retracting the plurality of needles into the cannula;
manipulating the handle to rotate the cannula and the needles into a second position within the patient; and
extending the plurality of needles through the apertures and expelling additional fluid from the plurality of needles.

12. The method of claim 11, further comprising:
again retracting the plurality of needles into the cannula;
manipulating the handle to rotate the cannula and the needles into a third position within the patient; and
again extending the plurality of needles through the apertures and expelling additional fluid from the plurality of needles.

13. The method of claim 11, wherein:
a first of the plurality of apertures is disposed on the right side portion of the distal end of the cannula;
a second of the plurality of apertures is disposed on the bottom portion of the distal end of the cannula; and
a third of the plurality of apertures is disposed on the left side portion of the distal end of the cannula.

14. The method of claim 13, wherein the cannula is configured such that no apertures are disposed upon an upper portion of the distal end of the cannula, and when the device is inserted in the first position the device is inserted into the patient's urethra with the upper portion of the distal end of the cannula facing upwardly when the patient is oriented in a lithotomy position.

15. The method of claim 11, wherein the device is configured to simultaneously inject fluid into various portions of tissue coaxially surrounding the urethra when in each of the first, second, and third positions, but avoid injecting into vessels and nerve bundles disposed proximate the urethra.

16. The method of claim 11, wherein the device further comprises a plurality of visually perceptible indicators configured to provide an indication of depth of insertion of the cannula within the patient, and further comprising the step of visually monitoring the depth of insertion of the cannula within the patient by observation of the plurality of visually perceptible indicators.

17. The method of claim 11, wherein the plurality of needles are configured to extend through a submucosa layer and into a muscle tissue coaxially surrounding a urethra when extended through the plurality of apertures.

18. The method of claim 11, wherein the fluid is a therapeutic agent.

19. A medical device comprising:
an elongate cannula comprising:
a distal end portion, wherein an outer circumferential surface of the distal end portion defines an upper portion, a right side portion, a bottom portion, and a left side portion each substantially equally spaced from their respective neighboring portion around the circumferential surface of the cannula;
a proximal end portion;
a lumen defined therethrough; and
a plurality of apertures disposed through the distal end portion to provide communication with the lumen, wherein a first of the plurality of apertures is disposed on the right side portion; a second of the plurality of apertures is disposed on the bottom portion; and a third of the plurality of apertures is disposed on the left side portion;
a plurality of injection needles disposed within the lumen, each comprising:
a distal portion disposed in alignment with the plurality of apertures; and
a proximal end portion;
a handle fixed with respect to the cannula, the handle comprising:
a housing configured to enclose syringe enclosing a fluid volume;
a shifter mechanism coupled to the proximal end portion of the cannula and the proximal end portion of each of the plurality of needles, the shifter mechanism translatable with respect to the housing to translate the plurality of needles from a first position to a second position, the shifter mechanism rotatable with respect to the handle to rotate the cannula with respect to the handle;
a slot defined in the housing configured to receive a portion of the shifter mechanism therethrough, the slot comprising a transversal track and a plurality of longitudinal tracks, wherein the transversal track defines a potential range of rotational motion of the shifter mechanism with respect to the housing, and each longitudinal track defines a potential range of translational motion of the shifter mechanism with respect to the housing between the first and second positions;
a conduit providing fluid communication between the syringe and the cannula; and
a syringe actuation mechanism comprising:
a thumbwheel;
a first tubular portion affixed to the thumbwheel; and
a second tubular portion configured to engage the first tubular portion and to partially receive the syringe;
wherein in the first position the distal portion of each of the plurality of needles is disposed within the lumen of the cannula;
wherein in the second position the distal portion of each of the plurality of needles extends out of the lumen through respective apertures; and
wherein rotation of the thumbwheel produces a translational motion of the second tubular portion towards the proximal end of the housing, urging expulsion of the fluid volume from the syringe and out of the needles.

20. The medical device of claim 19, wherein the cannula further comprises a plurality of visually perceptible indicators configured to provide an indication of depth of insertion of the cannula within a patient.

* * * * *